United States Patent
De Wolf et al.

(10) Patent No.: US 11,878,878 B2
(45) Date of Patent: Jan. 23, 2024

(54) CONNECTOR ASSEMBLY, SYSTEM AND METHOD FOR CONVERTING A BATCH WISE SUPPLY OF INSECTS TO A CONTINUOUS SUPPLY OF INSECTS

(71) Applicant: Protix B.V., Dongen (NL)

(72) Inventors: Lucius Petrus Cornelis De Wolf, Helmond (NL); Stijn Harms, Den Bosch (NL); Kees Wilhelmus Petrus Aarts, Vught (NL); Eric Holland Schmitt, Antwerp (BE)

(73) Assignee: Protix B.V., Dongen (NL)

( * ) Notice: Subject to any disclaimer, the term of this patent is extended or adjusted under 35 U.S.C. 154(b) by 93 days.

(21) Appl. No.: 17/615,606

(22) PCT Filed: Jun. 3, 2020

(86) PCT No.: PCT/NL2020/050356
§ 371 (c)(1),
(2) Date: Dec. 1, 2021

(87) PCT Pub. No.: WO2020/246879
PCT Pub. Date: Dec. 10, 2020

(65) Prior Publication Data
US 2022/0306404 A1    Sep. 29, 2022

Related U.S. Application Data

(60) Provisional application No. 62/858,338, filed on Jun. 7, 2019.

(30) Foreign Application Priority Data

Jun. 28, 2019 (NL) ..................... 2023406

(51) Int. Cl.
*B65G 51/01* (2006.01)
*B65G 47/19* (2006.01)

(52) U.S. Cl.
CPC ............. *B65G 51/01* (2013.01); *B65G 47/19* (2013.01); *B65G 2201/047* (2013.01); *B65G 2203/0258* (2013.01)

(58) Field of Classification Search
CPC .................................................. B65G 51/01
See application file for complete search history.

(56) References Cited

U.S. PATENT DOCUMENTS 3,260,548 A * 7/1966 Reichl .................... B65G 53/30
406/102
4,702,421 A * 10/1987 Wruck ................... B65G 53/30
44/280

(Continued)

FOREIGN PATENT DOCUMENTS

JP    S62269817 A1    11/1987
WO   2019125162 A1    6/2019

*Primary Examiner* — William R Harp
(74) *Attorney, Agent, or Firm* — N.V. Nederlandsch Octrooibureau

(57) ABSTRACT

Connector assembly (100), system and method for converting a batch wise supply of insects (102) to a continuous supply of insects (102). A container unit is present (105) having an internal volume, a water inlet unit (106-109, 117), and a suspension outlet unit (110-113). A receiving unit (101) has a top opening (101a) arranged for receiving batch wise quantities of insects (102) and a bottom opening (114). A conveyor unit (104) has a receiving part (104b) arranged near the bottom opening (114) of the receiving unit (101), and an outlet end (119) extending into the container unit (105). By suspending the insects (102) in water it is possible to transport the suspension of insects (102) in water, e.g. to a buffer container (300).

13 Claims, 7 Drawing Sheets

(56) References Cited

U.S. PATENT DOCUMENTS 7,677,397 B2 * 3/2010 Bjornson ............... B07B 1/155
　　　　　　　　　　　　　　　　　　　209/672
2006/0002191 A1 1/2006 Frey et al.

* cited by examiner

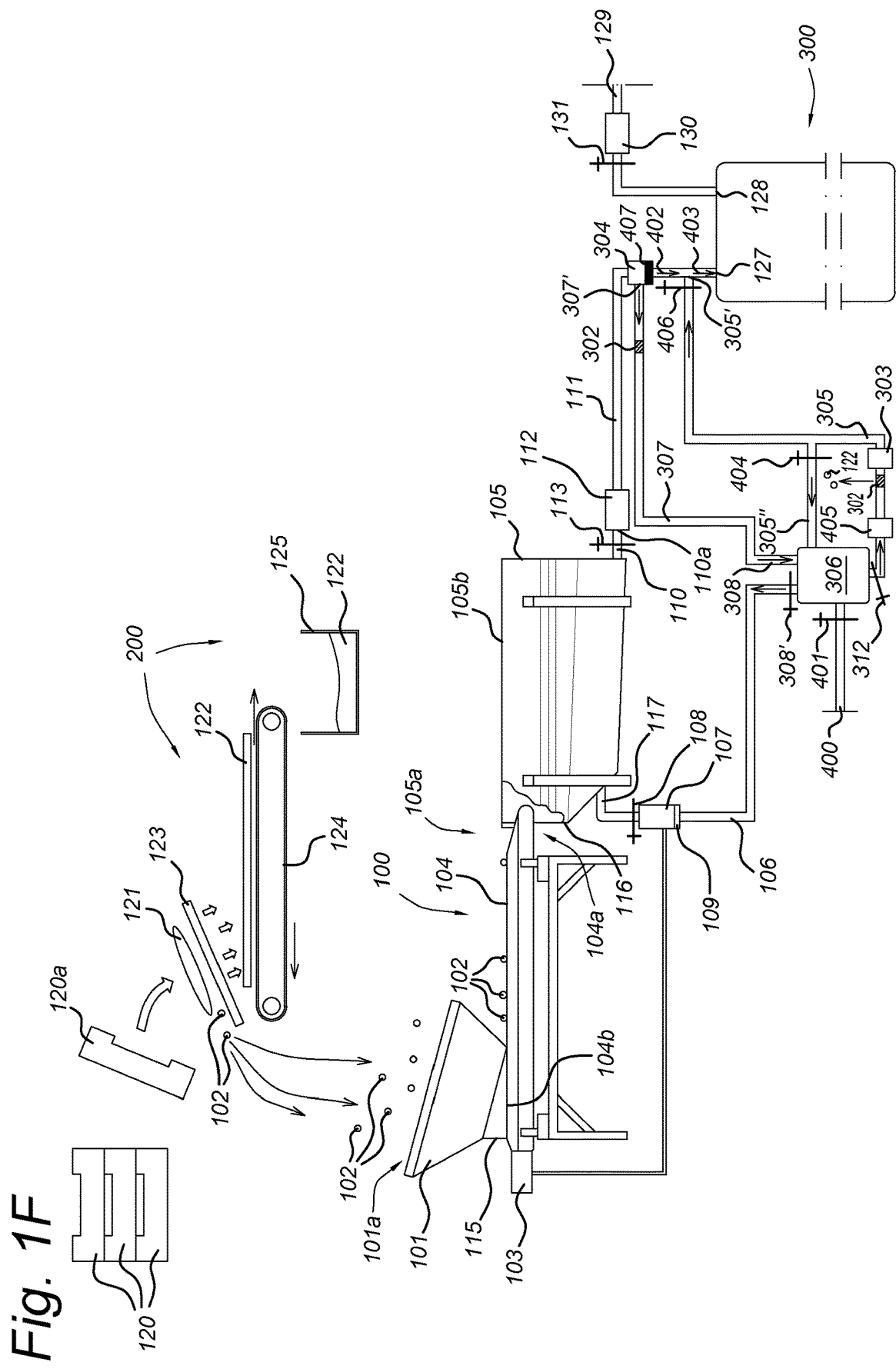

CONNECTOR ASSEMBLY, SYSTEM AND METHOD FOR CONVERTING A BATCH WISE SUPPLY OF INSECTS TO A CONTINUOUS SUPPLY OF INSECTS

FIELD OF THE INVENTION

The present invention relates to a connector assembly for converting a batch wise supply of insects to a continuous supply of insects, in a first aspect. In further aspects, the present invention relates to a system and method for converting a batch wise supply of insects to a continuous supply of insects

BACKGROUND ART

Insects are considered one of the most promising sources for fulfilling current and future demand for e.g. protein and fat. Prominent examples of species proposed for the indicated applications include the black soldier fly (*Hermetia illucens*), the house fly (*Musca domestica*), and the mealworm (*Tenebrio molitor* L.).

Methods for improving the efficiency of insect farming relating to improvements in insect processing and insect product production are particularly valuable for large scale production. This, because of the batch wise nature of the insect farming steps that should be performed and cannot be avoided while working with livestock, in order to be able to arrive at an economically viable scale. Despite the batch wise farming, or rearing of insects, for example insect processing into products desirably is a continuous process. In a continuous process, a manufactory for producing insect-based products is used efficiently, and no production capacity and production time is lost. Therefore, continuous use and processing of insects should preferentially not be hampered by batch-to-batch supply of ready-to-process insects. Since large-scale insect farming and subsequent insect processing into products is a desired industrial activity that involves live animals, a method and means for a continuous supply of insects would contribute to efficient use of farming facilities and insect processing facilities, and would aid in achieving predictable and controllable production volumes.

Thus, to the benefit of industrial-scale insect farming and subsequent industrial-scale insect-based product manufacturing, efficaciously and beneficially supplying insects in a continuous manner despite the batch-wise culturing steps involved in rearing insects, is an important requirement. However, methods and means to the benefit of said purpose are at present not available in the art.

Therefore, a solution still needs to be found that allows for feasible means for providing an uninterrupted supply of insects at economically sufficient large scale when industrial insect farming and industrial insect-based product production is considered.

SUMMARY OF THE INVENTION

The present invention seeks to provide an improved process for continuous processing insects in the production of e.g. insect-derived products.

Furthermore, the present invention seeks to provide a method and a system that allows for the continuous supply of insects to a manufactory for producing insect-based products, in view of the batch-wise supply of insects as a result of industrial-scale insect rearing.

According to the present invention, in a first aspect, a connector assembly is provided. The connector assembly is for converting a batch wise supply of live insects to a continuous supply of live insects, and includes a container unit having an internal volume, a water inlet unit, and a suspension outlet unit, a receiving unit having a top opening arranged for receiving batch wise quantities of live insects and a bottom opening, and a conveyor unit having a receiving part arranged near the bottom opening of the receiving unit, and an outlet end extending into the container unit. In a further aspect, a system is provided which includes the connector assembly and a separation unit positioned near the top opening of the receiving unit, the separation unit being arranged to provide batch wise quantities of insects to the receiving unit and to separate waste from the batch wise quantities of insects. In an even further aspect, a method for converting a batch wise supply of insects to a continuous supply of insects is provided.

The present invention will be described with respect to particular embodiments but the invention is not limited thereto but only by the claims.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The embodiments of the invention described herein can operate in combination and cooperation, unless specified otherwise.

Furthermore, the various embodiments, although referred to as "preferred" or "e.g." or "for example" or "in particular" are to be construed as exemplary manners in which the invention may be implemented rather than as limiting the scope of the invention.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, as an example, the scope of the expression "a receptacle comprising A and B" should not be limited to a receptacle consisting only of components A and B, rather with respect to the present invention, the only enumerated components of the receptacle are A and B, and further the claim should be interpreted as including equivalents of those components.

In addition, reference to an element by the indefinite article "a" or "an" does not exclude the possibility that more than one of the element are present, unless the context clearly requires that there is one and only one of the elements. The indefinite article "a" or "an" thus usually means "at least one".

SHORT DESCRIPTION OF DRAWINGS

The present invention will be discussed in more detail below, with reference to the attached drawings, in which FIG. 1A shows a perspective view of an embodiment of a connector assembly 100 for converting batch wise supply of insects to continuous supply of insects;

FIG. 1B is a top view of the connector assembly 100 for converting batch wise supply of insects to continuous supply of insects as shown in FIG. 1A;

FIG. 1C shows a schematic diagram of an embodiment of a system 200 for converting batch wise supply of insects to continuous supply of insects, comprising the connector assembly 100 for converting batch wise supply of insects to continuous supply of insects shown in FIGS. 1A and B, and further comprising an insect buffer container 300;

FIG. 1D shows an enlarged partial view of area 1D indicated in FIG. 1C;

FIG. 1E shows a schematic diagram of an embodiment of a system 200 for converting batch wise supply of insects to continuous supply of insects, comprising the connector assembly 100 for converting batch wise supply of insects to continuous supply of insects shown in FIGS. 1A and B, and further comprising an insect buffer container 300 and a water buffer container 310, wherein buffer container 300, water buffer container 310 and connector assembly 100 form a closed circuit 500 for circulating water from buffer container 300, to and through the water buffer container 310, back to connector assembly 100; and FIG. 1F shows a schematic diagram of an embodiment of a system 200 for converting batch wise supply of insects to continuous supply of insects, comprising the connector assembly 100 for converting batch wise supply of insects to continuous supply of insects shown in FIGS. 1A and B, and further comprising an insect buffer container 300 and a water buffer container 306, wherein the system 200 comprises a water circuit for circulating water from the connector assembly 100 to water buffer container 306 and back to the connector assembly 100, and wherein a water outlet tube 111 of connector assembly 100, buffer container 300 and water buffer container 306 form a second circuit for storing water which exits connector assembly 100 in water buffer container 306 and for transporting said water from the water buffer container 306 to an inlet of the buffer container 300;

DESCRIPTION OF EMBODIMENTS

Figure 1A:
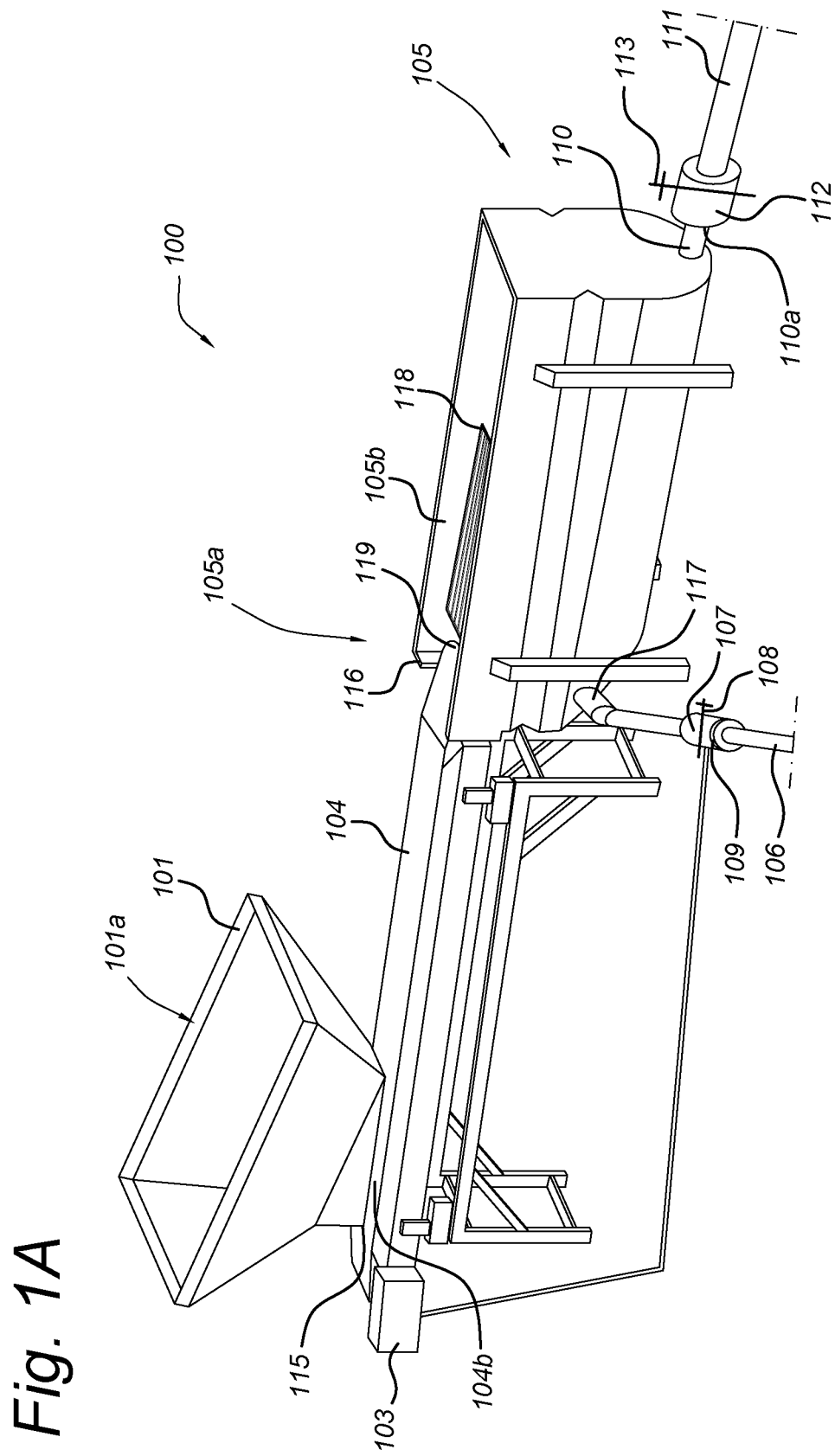
FIG. 1G shows a schematic diagram of an embodiment of an assembly 500 for transporting and storing larvae at varying transport- and storing liquid to larvae mass (:) mass ratio or volume (:) volume ratio.
FIG. 1H shows a schematic diagram of an embodiment of an assembly 600 for transporting and storing larvae at varying transport- and storing liquid to larvae mass (:) mass ratio or volume (:) volume ratio.

In generic terms, the present invention relates to a transport system for transporting animals such as insects or insect larvae, preferably living insect larvae such as larvae of black soldier fly, wherein the larvae are suspended in water and transferred from a first location to a second location by driving the larvae suspension through a tube, while the larvae stay physically intact and remain undamaged during transport. The invention also relates to a method for transporting animals such as larvae, wherein the method comprises the steps of weighing the larvae at a first location, suspending the larvae in an amount of water to a predetermined mass ratio animal (:) water, driving the obtained suspension of larvae in water through tubing or pipes to a second location. The invention further relates to a method for connecting a batch-wisely operating insect rearing farm with a continuously operating factory for processing the reared insects, such as an insect protein/oil production manufactory.

Advantages are achieved by providing a suspended insect transport system of the invention. At least an additional objective is achieved by providing a method for transferring suspended insects obtained from batch-wise mass insect rearing from a first location (e.g. the industrial scale insect farm) to a second location, e.g. a storage receptacle such as a bulk container. The bulk container fulfills the purpose of continuously supplying (feeding) a continuously operating insect-based product manufactory, by functioning as a buffer between the batch-wise production of insects at the first location and the continuously operating insect processing manufactory at the second location. The insects remain physically unaltered during transport and are undamaged upon the application of the transportation method. Moreover, the insects, such as black soldier fly larvae 12-22 days of age (preferably 13-20 days of age, more preferably 14-18 days of age such as 15 or 16 days of age, post-hatching) remain alive during larvae transport in water and thereafter, during subsequent storage in water for 30 minutes to 48 hours, such as 6 hours-24 hours, for example about 8 hours, 12 hours, 16 hours. Alternatively, some or all larvae die during bulk storage or even during preceding transport to the bulk storage receptacle, when the transportation method and subsequent bulk storage of larvae implies water at a temperature of below 10° C. such as 2° C.-8° C.

According to the invention, the preferred water temperature for transporting and storing larvae is 10° C.-20° C. The water can suitably applied at a temperature lower than 10° C. When the water temperature during transport and bulk storage is kept at 20° C. or lower, larvae are brought into hibernation and kept at hibernation. When the water temperature during transport and in particular during storage of the larvae is kept at 20° C. or lower, such as 10° C.-20° C., microbial growth is suppressed to an extent that is sufficiently efficient. When the water temperature during transport and bulk storage is kept at 20° C. or lower, any enzymatic activity in the bulk water, and at or in the larvae is minimal and to an extent that is sufficiently low such that the integrity and viability and the composition of the larvae is essentially unaltered at the end of the storage period compared to the composition at the start of the larvae transport. Storing the larvae in water with a temperature of about 20° C., such as 18° C.-24° C., is particularly suitable for subjecting the larvae to a subsequent processing step including mincing of the larvae, after the storage period of hours to e.g. 1-2 days. At about 20° C., enzymatic activity in and at the larvae is sufficiently low, the larvae are kept in hibernation, the larvae are kept alive during storage for up to e.g. 2 days (48 h), and processing of larvae implying mincing is efficiently possible. Larvae are kept alive in water for the indicated time span of up to two days if the water temperature during bulk storage in the receiving receptacle for bulk storage of transported larvae is for example 16° C. or higher, such as 16° C.-34° C., or 18° C.-26° C., such as ambient temperature or room temperature or 20° C.-24° C. Beneficially, during transport of suspended larvae in water and upon subsequent storage in water, the larvae are washed and cleaned such that for example excrements remains and feed substrate remains of rearing the insects, are at least partially washed from the bodies of the larvae. Typically, when larvae such as black soldier fly larvae 14-16 days of age are harvested and subjected to the transportation method of the invention, about up to 10% of the mass of the harvested batch of insects consists of feed substrate based on the total weight of the batch of insect larvae. The bulk of the feed substrate in which the larvae were reared is separated from the larvae and discarded before the larvae are subjected to the transport water.

In general terms, the present invention embodiments relate to a connector assembly 100 for converting a batch wise supply of insects 102 to a continuous supply of insects 102, comprising a container unit 105 having an internal volume, a water inlet unit (e.g. implemented as components 106-109, 117 described below), and a suspension outlet unit (e.g. implemented as components 110-113 described below). A receiving unit (such as the insect receiving receptacle described above) 101 is present having a top opening 101a arranged for receiving batch wise quantities of insects 102 and a bottom opening 114. A conveyor unit 104 is present having a receiving part 104b arranged near the bottom opening 114 of the receiving unit 101, and an outlet end 119 extending into the container unit 105.

In a further embodiment, the conveyor unit 104 further comprises a weighing device (e.g. a scale or a weighing belt, such as a dynamic or in-motion continuous-process weighing conveyor scale) 103 for measuring the quantity of insects on the receiving part 104b. As during operation of the connector assembly 100, a steady stream of insects 102 is moving on the conveyor unit 104 from receiving part 104b to the outlet end 119, the weight measurement can be executed in a dynamic manner.

FIG. 1A displays a three-dimensional connector assembly 100 for converting batch wise supply of insects to continuous supply of insects, comprising an insect receiving receptacle (or receiving unit) 101 for receiving batch-wisely produced insects 102, the insect receiving receptacle 101 being placed onto a weighing device such as a scale 103 or an in-motion weighing conveyor scale for weighing received insects 102 in the receiving receptacle 101, a conveyer unit 104 (e.g. a conveyor belt) for transporting weighed insects 102 to a container unit (or water bath) 105, the water bath 105 being connected to a water-inlet tube 106 for supplying water to the water bath 105, the water-inlet tube 106 being further provided with a water inlet control unit (controller) 107 connected to the scale 103, for controlling a valve 108 and a driver 109, the water bath 105 further being provided with a water-outlet opening 110 connected with a water-outlet tube 111, the water-outlet tube 111 being provided with a pumping device (or pump/driver) 112 for driving a suspension of insects in water through the water-outlet tube 111, the pump 112 e.g. being provided with a valve 113 for opening/closing water-outlet tube 111. So, in a further embodiment, the suspension outlet unit 110-113 comprises a pumping device 112, e.g. implemented as an expeller pump, not damaging the insects 102 in suspension.

The water provided to the water bath 105 through inlet opening 117 is typically and preferably cool water at a temperature below ambient temperature or below room temperature (17° C.-26° C.), such as water at a temperature of between 0° C. and 16.5° C., or for example 4° C.-12° C., or 6° C.-11° C., for example about 8° C.-10° C. Typically, the water temperature is selected between about 10° C. and about 20° C. for reasons outlined before here above. The water temperature is for example about 9° C. Suspending the insects, e.g. fly larvae such as mature larvae of black soldier fly, in water at a temperature of below 13° C., such as 7° C.-10° C., contributes to the prolonged stability, integrity, and the freshness and shelf life of the larvae, during e.g. temporarily storage for 0.5-2.5 days after suspending the larvae. The application of (cooled) water at a temperature of e.g. below 10° C. also contributes to prevention of decomposition of the larvae. Of course, keeping the water in which the larvae are suspended continuously actively (e.g. by stirring, swirling, tumbling, rotating) at such a temperature below room temperature further contributes to these beneficial results of cooling larvae suspension. All in all, the improved prolonged stability, integrity, and the freshness and shelf life of the larvae in such relatively cool water, compared to a suspension of larvae in water kept at a temperature higher than e.g. 15° C. (room temperature, ambient temperature, e.g. a temperature higher than 20° C.) contributes to a stable quality of the larvae and therewith to a stable source of larvae derived products such as proteins and lipids and fats, upon processing of the larvae, although keeping the larvae in water at e.g. room temperature also provides for sufficiently stable, integer and fresh larvae within the time span of e.g. 2-3 hours to 2-3 days, and the shelf life of the larvae kept in water at e.g. 18° C.-24° C. is also such that the larvae are of a adequately stable quality and therewith the larvae kept in water at higher temperature than 15° C., for example up to 20° C., are also a stable source of larvae derived products. Typically, the water is tap water such as regular tap water as provided to households in The Netherlands. Alternatively, the water is process water suitable for application in the food industry. The water is for example sieved and/or filtered ground water. For example, the water is sterilized water. The skilled person will appreciate that any source of water is suitable, if such water is applicable in a process for manufacturing feed stuff or food products.

Figure 1B:
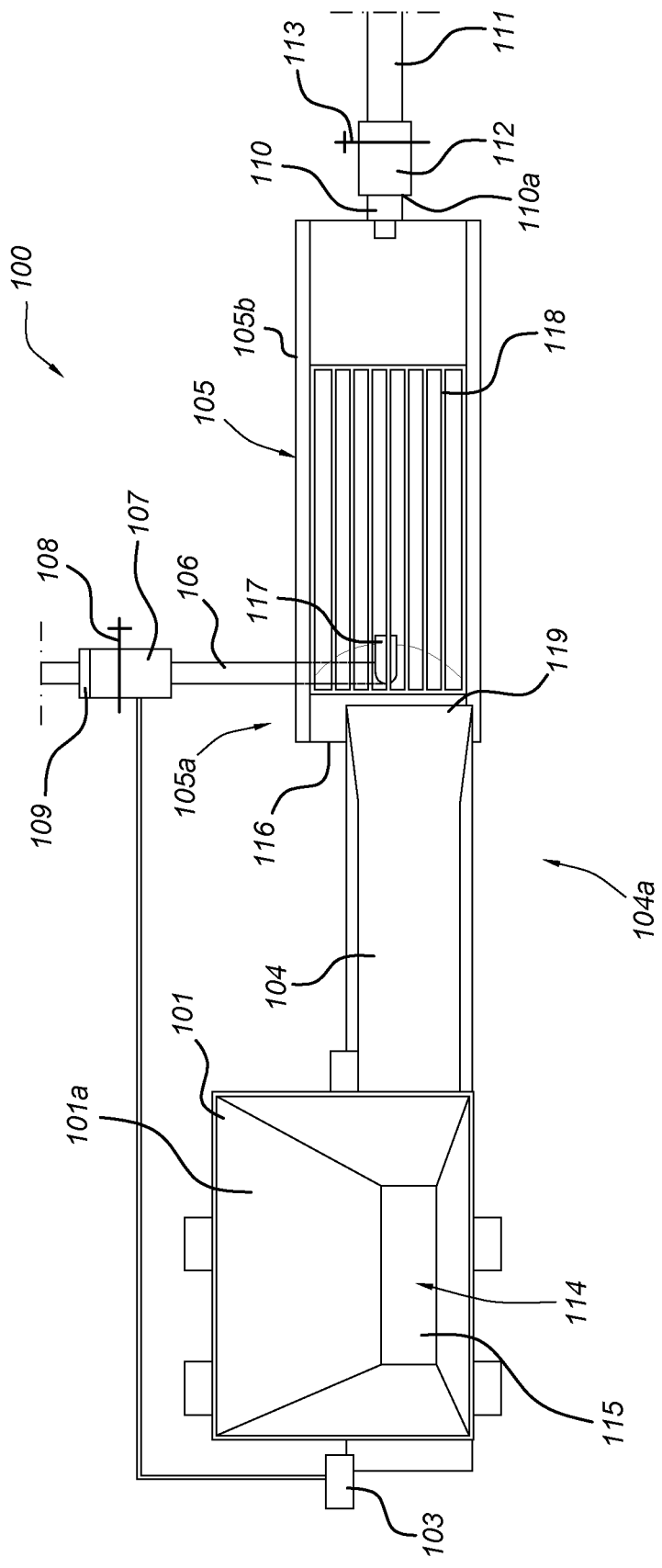

FIG. 1B is a top view of the connector assembly 100 for converting batch wise supply of insects to continuous supply of insects of FIG. 1A. Displayed is the tapered insect receiving receptacle 101 which is provided with a bottom opening 114 at the bottom portion 115 of the receptacle 101. Underneath the opening 114, the conveyer belt 104 is located, extending to the side portion 116 of the water bath 105. The water inlet tube 106 is connected with the water bath 105 at opening 117, and the water outlet tube 111 is connected to the water bath 105 through opening 110. Controller 107 connects the scale 103 with the water-inlet tube 106, and controls the valve 108 and driver 109.

The container unit (water bath) 105 is provided with an insect spreading element 118 (e.g. a grid) located at least underneath the end portion 119 of the conveyer belt 104. The grid 118 can further be arranged for preventing large particulates other than desired insects 102 from entering the water in the water bath 105. Water-outlet tube 111 is connected to the water bath 105 through connector 110a, and is provided with driver 112 for driving suspended insects in water through the water-outlet tube 111.

Figure 1D:
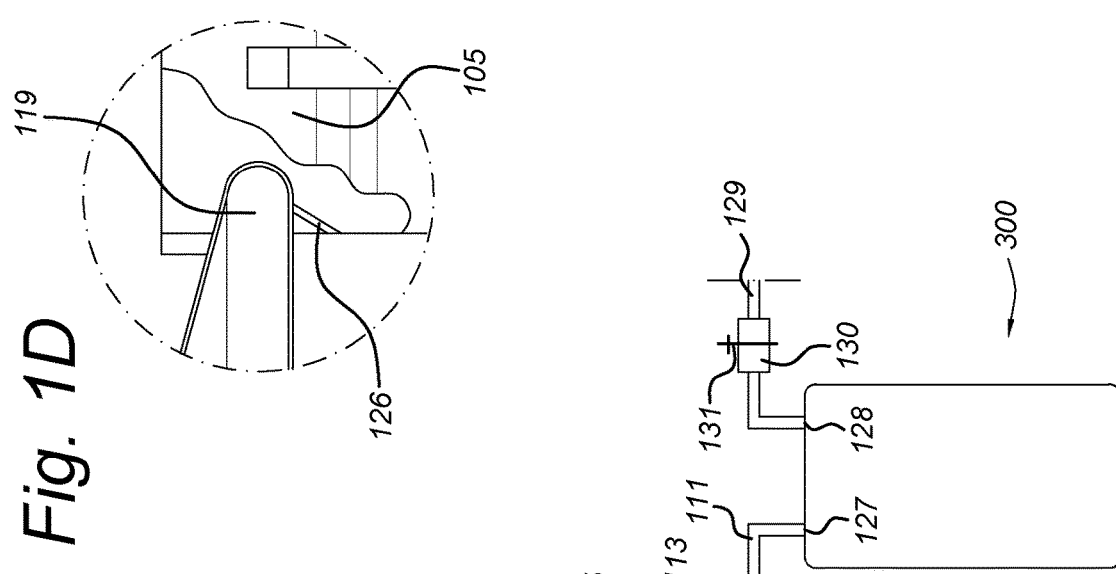
Figure 1C:
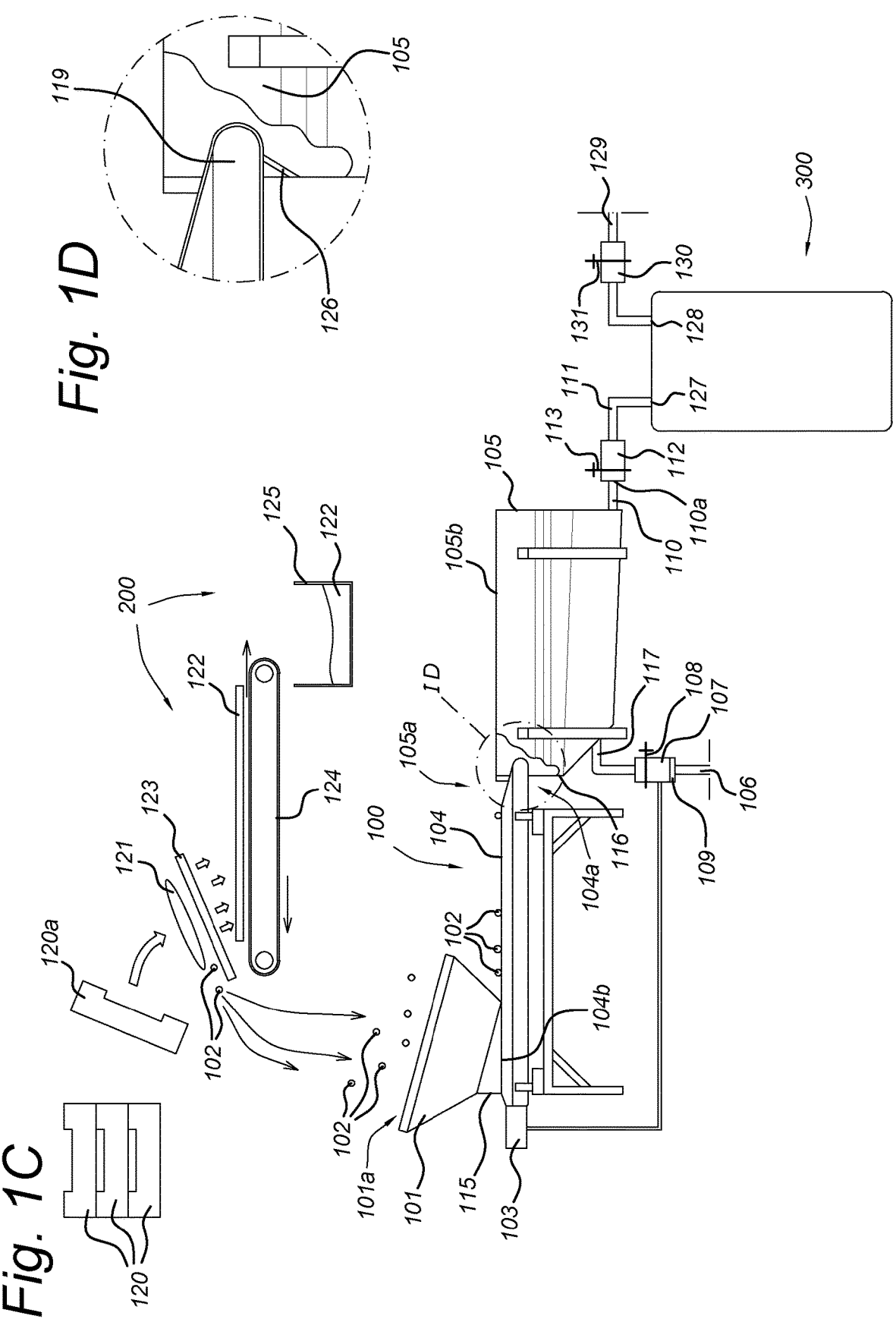

FIG. 1C shows a schematic diagram of a system 200 for converting batch wise supply of insects to continuous supply of insects, comprising the connector assembly 100 for converting batch wise supply of insects to continuous supply of insects displayed in FIGS. 1A and B. The system 200 represent a further aspect of the invention, comprising a connector assembly 100 according to any one of the embodiment described herein, further comprising a buffer container 300 connected to the suspension outlet unit 110-113. In further embodiments, the system 200 further comprises a separation unit 123 positioned near the top opening 101a of the receiving unit 101, the separation unit 123 being arranged to provide batch wise quantities of insects 102 to the receiving unit 101 and to separate waste (e.g. feed substrate remains) from the batch wise quantities of insects 102. Stacked crates 120, 120a comprising batch wisely reared insects 102 e.g. provide a batch wise supply of a combination 121 of insects 102 and waste 122 such as superfluous feed, excrements, remains of molting of the insects, etc. The crates 120, 120*a* are emptied on a separation unit (or sieve) 123 such as a vibrating screen 123 or a shaking sieve 123. Waste 122 is disposed on conveyer belt 124 and e.g. discarded in waste container 125. Insects 102 are collected in the insect receiving receptacle 101, positioned on scale 103. The scale 103 is connected to controller 107, this controller 107 connected to and controlling pump 109 and valve 108.

The conveyer belt 104 underneath the bottom opening 114 of the insect receiving receptacle 101 ends at one end portion 105*a* above the top opening 105*b* of water bath 105, for disposing insects through grid 118 and into the water in the water bath 105. A scraper 126 (see FIG. 1D) is located at the bottom side 104*a* of the end portion 119 of the conveyer belt 104, for discarding any adhered insects 102, etc. from the conveyor belt 104. Thus, in a further embodiment of the present invention, the conveyer unit 104 further comprises a scraper device 126 positioned near the outlet end 119.

The water bath 105 is fed with water through opening 117 connected to water-inlet tube 106. Feeding the water bath 105 is under control of controller 107, connecting the scale 103 and valve 108 and driver 109. In a further embodiment of the present invention, the water inlet unit comprises a water inlet control unit 107 connected to the weighing device 103 and arranged to control an amount of water supplied to the container unit 105 based on measurement data from the weighing device 103, in order to provide suspension of insects in water in the container unit.

The insect suspension is driven through water outlet tube 111 through opening 110 in the water bath 105, by a pumping device or pump 112. Pumping of the suspension of insects 102 in water can be enhanced when the suspension has a relatively constant insect content. To that end, in a further embodiment of the present invention, the container unit 105 comprises an inlet opening 117 and a suspension outlet opening 110 which are arranged asymmetrically with respect to a bottom part of the container unit 105. The asymmetric arrangement will result in a mixing action during operation in the internal volume of the container unit 105 to get an enhanced and continuous suspension of insects 102 in water. In addition or alternatively, the container unit 105 comprises an agitation device positioned in the internal volume of the container unit 105. Agitation of the larvae which are deposited in the container unit 105, in the volume of water comprised therein, such that the larvae suspension in water is formed, contributes to the rapid and even and constant provision of the predetermined larvae suspension with regard to volume and larvae to water mass ratio. By agitation of the water and the larvae suspension, 'dilution' of the larvae in the water is rapidly achieved and therewith the larvae suspension can be transported further within short time after entering the container unit 105, e.g. transfer to the buffer container 300 (see below), within a shorter time span from entering the container unit 105 up till achieving the sufficiently diluted larvae suspension, than when agitation is omitted. Agitation of the water entering the container unit 105 comprising the larvae in water also facilitates the maintenance of the larvae suspension at a constant and equal distribution and partitioning of larvae in the volume of water, therewith preventing accumulation, clustering and the settling of suspended larvae at the bottom of the container unit 105. The inventors established that transportation of larvae in suspension is harmlessly possible when keeping the larvae undamaged is considered, when the mass ratio of larvae to water is at most 1:1, or lower. That is to say at most, the mass of larvae is equal to the mass of water in the larvae suspension, or lower. Good results are achieved when the mass ratio of larvae to water during transportation of the larvae is between 1:2 and 1:50, and preferably, during transportation of the suspended larvae, the ratio is 1:20 or higher. Agitation prevents (local) clustering and accumulation of larvae in a (local) volume of water, and therewith contributes to preventing occurrence of damaged larvae upon suspending and transporting and storing the larvae.

The system 200 also comprises an insect buffer container 300. The insect suspension in water is driven into insect buffer container 300 through connector 127. The container 300 is provided with an outlet opening 128 connected to tube 129, for continuously transferring larvae suspension under control of driver 130 and controllable valve 131. The buffer container 300 has for example a capacity of containing 2-200 tons of insect larvae suspension in water, such as between 5 tons and 100 tons, or for example between 10 tons and 60 tons, such as 20 tons, 30 tons, 40 tons, 50 tons of larvae in water suspension.

Typically, the system 200 for converting batch wise supply of insects to continuous supply of insects is applied during rearing and breeding of insects, such as insect larvae, for example larvae of black soldier fly 10-25 days of age, preferably 13-17 days of age, and subsequent processing of said insects 102, such as larvae, into products derivable therefrom. As said, the rearing of insect larvae is by nature a batch wise process. Of course, manufacturing products using insect larvae as a source of raw materials is possible also in a batch wise manner, although a continuous production process is preferred at least from an economic perspective. Connecting the batch wise supply of livestock to the continuous production process of providing insect derived products is thus required. The system 200 is fed with the combination of larvae and accompanied feed remains, etc., typically by the provision of crates 120, 120*a* comprising said combination. Typically, a crate 120, 120*a* comprises about 500 gram-2.5 kg of larvae.

In a further aspect of the present invention, a method is provided for converting a batch wise supply of insects 102 to a continuous supply of insects 102, comprising providing batch wise quantities of insects 102, converting the batch wise quantities of insects 102 into a continuous stream of insects 102, suspending the continuous stream of insects 102 in water to obtain a suspension of insects 102 in water, and transporting (e.g. pumping) the suspension of insects 102 in water.

Crates 120, 120*a* are emptied manually or are emptied in an automated manner on the sieve 123, for example by applying robotics (not shown). Typically, stacks of crates 120 are provided, the crates 120, 120*a* comprising a combination of insect larvae 102 such as black soldier fly larvae of for example about 18-23 days of age post hatching, preferably 12-18 days of age, and remaining feed, larvae excrements, remains after molting of the larvae, etc. 122. The mix of larvae 102 and waste 122 is separated in a larvae fraction comprising predominantly the larvae 102 when the mass ratio larvae (:) waste is considered, and a waste 122 fraction typically consisting of particles with a size smaller than the e.g. black soldier fly larvae. The waste fraction 122 is discarded, for example by the application of a conveyer belt 124, transporting the waste fraction 122 to a bin 125 such as a waste container 125. Thus, a further method embodiment comprises separating waste 122 from the batch wise quantities of insects 102. The waste fraction that remains with the larvae 102 accumulates to at most 10% based on the total weight of the larvae and waste (predominantly feed substrate remains).

The insects 102 such as larvae are separated from the waste 122 and are introduced in the receptacle 101, such as a tapered receptacle 101, such as a funnel 101, the tapered receptacle 101 having an opening 114 in the bottom portion 115 of the receptacle, such as a rectangular opening 114 or a slit 114. The scale 103 positioned underneath the receptacle 101 continuously weighs the larvae 102 that contact the conveyer belt 104. Based on the amount of larvae 102 that is weighed, for example weighed per time unit (for example gram/minute), the controller 107 controls valve 108 and driver 109 such that an amount of water enters the water bath 105 per time unit through pipe 106 and opening 117, resulting in a controlled and predetermined and constant provision of a suspension of insects in water, such as insect larvae 102 in water, when the mass ratio of insects (for example including a minor portion waste remains, e.g. adhered to the insects, consisting of for example less than 12% by weight of the total weight of weighed insects including adhered waste, such as 0.1%-4% by weight, or less than 2% by weight, or typically 10% or less)) to water is considered. Thus, in a further method embodiment, the method further comprises controlling an input volume of water depending on the weight of insects 102 to be suspended in the water. In an even further embodiment, the method further comprises spreading the continuous stream of insects 102 over a surface of the water (in the container unit 105), in order to obtain an even spread and consistent suspension of the insects 102 in the water. This may even be further enhanced in a further method embodiment comprising agitating the suspension of insects 102 in the water.

The mass ratio between insects (e.g. black soldier fly insect larvae) and water is selected such that the insects 102 are not damaged when suspended in water bath 105 and when once being pumped from the water bath 105 comprising the insect suspension, through lining 111, to the buffer container 300. Typically, the mass ratio insect larvae (:) water in the pumpable suspension is 0.02 (:) 1 to 0.7 (:) 1, for example between 0.05 (:) 1 and 1 (:) 1, or between 0.07 (:) 1 and 0.7 (:) 1, such as 0.1 (:) 1 or 0.2 (:) 1 or 0.5 (:) 1. For example, the ratio amounts to about 75 gram insect larvae admixed with 1 liter water, or about 150 gram insect larvae admixed with 1 liter water, or about 300 gram insect larvae admixed with 1 liter water, or about 650 gram insect larvae admixed with 1 liter water. In water bath 105, an amount of water is constantly present and fed to the water bath, such that the larvae 102 which are fed to the water bath by the conveyer belt 104, are suspended in the water bath at a typical mass ratio of one part larvae such as black soldier fly larvae and 7-13 parts water, for example 10 parts water. For example, the water temperature is 6° C.-13° C., such as about 9° C. or 11° C., when fed to the water bath. It is important to keep the suspended insects such as insect larvae for example those of black soldier fly intact, uninjured and undamaged, for the purpose of storing the suspended larvae, for, for example up to 10-30 hours, or for 12-60 hours, such as 16-48 hours, in water, and for keeping the quality of any products derived from the larvae constant and at a suitable level. For example, larvae reared for the purpose of retrieving oil and/or proteins from them would become useless for the purpose of processing such larvae, when these larvae would become damaged due to transportation and storage, before the processing of such larvae, such that some larvae oil is spilt at best, or completely lost by contacting damaged larvae with water before processing. In addition, if insects such as black soldier fly larvae require a washing step before processing for retrieving for example oil, for example to discard substrate or faeces adhered to the exterior of the larvae, such washing step would be severely hampered when larvae are damaged, partitioned, etc. before the washing step, since upon the washing step, some if not all oil would be washed away before processing was possible. It is now due to the present invention embodiments that these drawbacks do not occur when the connector assembly 100 or the system 200 comprising the connector assembly 100 is applied with living larvae. Application of the system 200 thus combines the provision of a means to transfer the batch wise rearing of larvae to a continuous supply of (living) larvae, whilst the larvae keep their body integrity (i.e. without damaging, wounding, partitioning, etc.). Moreover, the larvae stay alive. During transport of the larvae suspension and/or during bulk storage, the water temperature is 12° C. or below such as 1° C.-12° C., or the water temperature is above 12° C. such as ambient temperature or room temperature, such as 17.5° C. — 23.5° C., or 19° C. — 22.5° C., and preferably the water temperature is at or below 20° C. such as 10° C.-20° C.

Typically, the driver 112 drives between 500 kg larvae per hour, suspended in 800-10.000 liter water, and 12.000 kg larvae per hour, suspended in 16.000-250.000 liter water, from the water bath 105 through tubing 111 to the second location, for example to storage container 300, which functions as a buffer container, receiving suspended larvae. For example, 2.000-9.000 kg larvae suspended in 7.000-100.000 liter water, are transferred undamaged to the buffer container 300, under influence of operating driver 112. For example, continuously driver 112 drives the suspension of larvae in water to the buffer tank 300 at an amount of about 3.600 kg/hrs larvae suspended in about 40.000 liter water per hr (suspension is for example transported from the water bath to the buffer tank at about 44.000 kg/hr or about 44 m$^3$/hr) The flow rate is typically 5-22 l/sec, such as about 9 l/sec, 12 l/sec, 15 l/sec, 18 l/sec. Typically, for example between 10 kg and 180 kg larvae are transported per minute from the water bath 105 to the buffer container 3000, such as about 30 kg/min, 60 kg/min, 90 kg/min. In the buffer container 300, the suspended larvae are typically diluted with cold water (2° C.-11° C., such as about 7° C.-10° C., for example about 9° C.) to a final storage mass ratio between larvae and water of between 1 (:) 1 and 1 (:) 5, or between 0.7 (:) 1 and 0.15 (:) 1, for example 0.5 (:) 1, or 0.2 (:) 1. As a result of the selected and controlled mass ratio between larvae and water in the suspension, and as the result of the pressure applied to the transported larvae suspension in water, e.g. 1-3.5 bar such as about 1,4-2.8 bar, for example about 2 bar, the larvae remain intact in the water bath, during transfer from the water bath to the buffer tank (buffer container 300), and during storage in the buffer tank for about 15-30 hours such as about 18 hours, 22 hours. During transport of the larvae suspension and/or during bulk storage, the water temperature is 12° C. or below such as 1° C.-12° C., or the water temperature is above 12° C. and below 20° C., or is at ambient temperature or room temperature, such as 17.5° C.-23.5° C., or 19° C.-22.5° C.

The continuous batch wise supply of larvae 102 from the crates 120, 120a into the water bath 105, therewith providing larvae suspended in water, due to the operation of the connector assembly 100, connects the batch wise insect rearing process to the continuous transport of suspended larvae from the water bath 105 to receptacle 300 (buffer container 300). The buffer container 300 serves as an enlarged buffer and receptacle for receiving and temporarily (10-40 hours, such as about 24 hours) storing suspended larvae until further processing. Suspended larvae are transported for example by driver 130 through opening 128 of the buffer container 300 connected to tubing 129, once valve 131 is opened and driver 130 turned on in pump modus. For example, the transport of suspended larvae in water at a mass ratio of between 1 part larvae and 2 parts water and 1 part larvae and 5 parts water, or at a mass ratio of about 1 part larvae and 1 part water, is at a mass transfer rate of about 1000 kg/hr-5.200 kg/hr when larvae are considered, wherein it is of course appreciated that the transport of larvae from the bulk container 300 to e.g. a processing unit (not shown) through tube 129 exiting the bulk container 300, is at a lower larvae mass rate in kg per time unit than the larvae mass rate in kg per time unit, entering the buffer container 300 through opening 128, fed from water bath 105, in order to ensure the continuous supply of suspended larvae to the larvae processing manufactory. For example, the buffer container 300 is continuously filled with larvae suspension in water at 2.000-5.000 kg larvae per hour (suspended in for example 18.000-100.000 liter water) from the water bath 105, whereas the buffer container 300 is for example continuously emptied at 1.000-3.500 kg larvae per hour (suspended in for example 1.800-25.000 liter water) through opening 128, by operating driver 130 and opening valve 131. Of course, buffer container 300 can also be filled with larvae suspension, after which the suspension is stored for, for example, 1 day, followed by further transport of the larvae to a larvae processing unit, when for example more than one buffer containers 300 are filled in parallel or subsequently and the larvae processing is fed from a first, filled buffer container, while a second buffer container is filled, followed by feeding the larvae processing from the second, then filled buffer container while the first buffer container is again re-filled, etc., etc.

Operating the connector assembly 100 with black soldier larvae results in the larvae remaining physically undamaged when suspended in water bath 105, and when subsequently transported through tubing or pipe 111. Moreover, by operating the connector assembly, the batch wise provided larvae stay alive when suspended in water for at least 1-2 days, such as about 20-36 hours, typically at least 24 hours, such as 24, 26, 28 hours. During storage of suspended larvae, the larvae stay intact and are not damaged nor injured upon suspending and storing and transferring from a first location such as a larvae farm to a second location such as a bulk storage container such as buffer container 300. Due to the selected combination of applied pressure applied onto the suspension in tubing 111 (1-2.5 bar, typically, such as about 2 bar) and mass ratio between larvae and water in the larvae suspension of typically between 1(:)13 and 1(:)1.5, such as between 1(:)10 and 1(:)2, or about 1(:)5, and selected suspension transfer rate of about 20.000-80.000 kg/hr, for example about 35.000-55.000 kg/hr when transfer of suspension from the first location, i.e. the water bath 105 comprised by the connector assembly 100, to the second location through tubing 111, e.g. the buffer container 300 comprised by system 200, is considered, insects such as black soldier larvae remain undamaged and for example remain alive during suspending the larvae, collecting the larvae in water bath 105, transporting the suspended larvae through tubing 111, and during storage of suspended larvae in buffer container 300.

The buffer container 300 is optionally provided with a temperature insulating coating or layer, and/or is manufactured from a heat insulating material, for improved control of larvae suspension temperature kept in the buffer container.

Figure 1E:
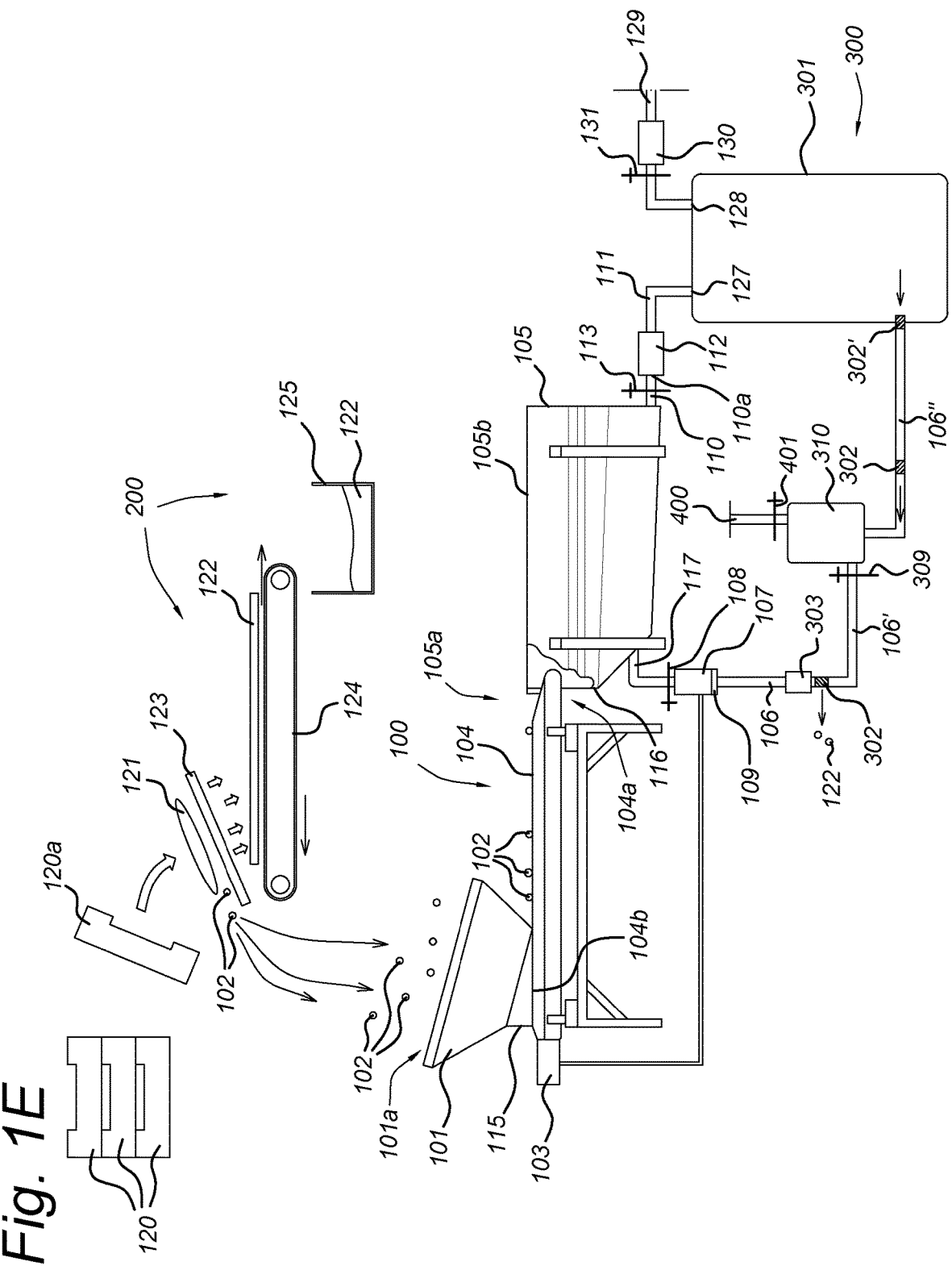

FIG. 1E shows a schematic diagram of an embodiment of the system 200 for converting batch wise supply of insects, such as black soldier fly larvae, to continuous supply of insects, comprising the connector assembly 100 for converting batch wise supply of insects to continuous supply of insects displayed in FIGS. 1A and B and comprising the buffer container 300. The buffer container 300 is optionally insulated with a layer of an insulating material 301, such that the temperature of the insect (e.g. larvae) suspension stored in the buffer container is improvingly controllable and improvingly kept stable at a selected temperature, preferably at a temperature of between 10° C. and 20° C.

The buffer container 300 is optionally connected with the connector assembly 100 via a water outlet tube or pipe 106", tube or pipe 106' and the water-inlet tube 106 for supplying water to the water bath 105, the water-inlet tube 106 being further provided with a water cooling unit 303 for optionally cooling of the water provided from the buffer container 300 to the water bath 105, for example to a temperature of about 10° C.

In an embodiment the tube 106" is provided with separation means 302' for separating larvae and water, at or near the position where tube 106" exits buffer container 300. The separation means 302' is for separating larvae and water, thus keeping larvae and a fraction of the water inside buffer container 300 and transferring the remainder of the water from buffer container 300 into tube 106", depleted from larvae. The separation means 302' is for example a filter, a sieve, a gauze, a maze, a net, with openings sufficiently small to retain larvae inside buffer container 300 while water is flowing into tube 106" through separation means 302'.

In an embodiment the separation means 302' is optionally controllable, for example with a tap or valve encompassed by the separation means. The tube 106" and/or the tube 106' is optionally provided with a filter means 302 for freeing the water from any solid matter 122 suspended therein. The filter means 302 is for example a filter, a sieve, a gauze, a maze, a net, with openings sufficiently small to hold the solid matter 122, while water is flowing through tube 106" and tube 106', thus through filter means 302. Solid matter 122 is discarded from the filter means 302.

In an embodiment, tube 106" is optionally provided with a driver such as a pump, for driving the water towards pipe 106', optionally first to and through buffer container 310. Tube 106" and/or tube 106' comprise a valve 309 for controlling the flow of water from buffer container 300 back to water bath 105 and/or for controlling the amount, timing, flow velocity of the flowing water.

In an embodiment, the water exiting buffer container 300 through tube 106" is collected in a second buffer container 310 for storing and transporting water. The second buffer container 310 allows for improved control of the water flowing through the circuit formed by connector assembly 100 and buffer container 300, both with regard to amount and flow velocity. Since part of the water that enters buffer container 300 from connector assembly 100 can be kept in buffer container 300, for storing and further transporting larvae at higher larvae density in the remaining water, while a fraction can exit buffer container 300 through tube 106".

In an embodiment, the second buffer container 310 or tube 106" or tube 106' or tube 106 is optionally connected with a water inlet pipe 400 for adding water to the water circuit formed by water bath 105, tube 111, buffer container 300, tube 106", optionally second buffer container 310, tube 106' and pipe 106. This allows for concentrating the larvae entering the buffer container 300 via pipe 111, and re-using the water retrieved from the more diluted larvae suspension made in water bath 105, for transporting the water back to water bath 105. The concentrated larvae in buffer container 300 can be further transported via outlet 128 to tube 129.

In an embodiment, the water inlet pipe 400 for adding external water to the circuit and to the second buffer container 310 is provided with a valve 401, for controlling the amount and flow of water that flows to water bath 105. Thus, this way, a closed circuit for circulating water from water bath 105 to buffer container 300 and back to water bath 105 is established. The water inlet tube 106 is thus optionally provided with a filter 302 for filtering water exiting the buffer container 300, before the water enters the water bath 105. Debris 122 is disposed from the filter 302 in water inlet tube 106. This way, purified water free of debris enters water bath 105, for suspending the batch-wise delivered larvae by the connector assembly 100. The water in the system 200 is maximally re-used by recirculating superfluous water from buffer container 300 back to water bath 105. Suspended larvae transported through tube 129 are typically brought to a higher larvae to water density compared to the larvae to water density during transport, such that excess water is available for re-circulating through water inlet tube 106. For example, larvae are transported from water bath 105 to buffer container 300 at a density of 1 part larvae and 20 parts water based on the weight of the water, whereas during transport from the buffer container 300 through tube 129, the larvae are transported at a density of 1 part larvae and between 2 and 5 parts water based on the weight of the water.

FIG. 1F shows a schematic diagram of an embodiment of the system 200 for converting batch wise supply of insects to continuous supply of insects, comprising the connector assembly 100 for converting batch wise supply of insects to continuous supply of insects displayed in FIGS. 1A and B and comprising the buffer container 300, and further comprising optional features.

In an embodiment, the water outlet tube 111 that connects the water bath 105 with the buffer container 300 is optionally provided with a filter means 304 for separating suspended larvae from water, such as a sieve, a gauze, a net, a filter, for example a rotating drum screen 304. Before suspended larvae are transported and delivered into the buffer container 300, the larvae are separated from the transport water by application of the filter means 304. The amount of filtered and isolated larvae 402 after passing filter means is optionally determined (on a weight basis or on a volume basis) with means for determining larvae mass or volume 407 that is located downstream of filter means 304. Based on the determined amount of isolated larvae 402 (mass or volume or both), a defined and controlled amount of (filtered) water is mixed with the isolated larvae 402, such that the mass or volume ratio larvae to water is higher after filtration and resuspension of the resuspended larvae 403 than before the filtering using filter 304: for example, suspended larvae exiting water bath 105 are suspended at 1 part larvae and 10-50 parts water, and suspended larvae 403 entering buffer container 300 after filtering with filter 304 and resuspension thereafter, are suspended for example at 1 part larvae and 1-8 parts water, such as 2-5 parts water. The water that is separated from the larvae with sieve 304 is exiting water outlet tube 111 through connector 307' via pipe 307. Pipe 307 connects outlet tube 111 with water inlet tube 106 of water bath 105, therewith establishing a water circuit between water inlet control unit 107 and connector 307' and water outlet tube 111. The remaining fraction of the transport water exiting the water bath 105 and separated from the suspended larvae by filter 304, that is not (immediately) re-used for resuspending in water the separated filtered larvae 402 after filtering by filter 304, is re-used for suspending further larvae 102 in water bath 105. A fraction of the water filtered with filter 304 is optionally collected and (temporarily) stored in receptacle 306 such as a water tank 306 such as an insulated water container 306 or second water buffer container 306. Receptacle 306 is supplied with the fraction of the filtered water through pipe 307 and connector pipe 308 which connects pipe 307 with receptacle 306.

Since part of the water that enters buffer container 300 from connector assembly 100 can be kept in buffer container 300, for storing and further transporting larvae at higher larvae density in the remaining water, while a fraction can exit buffer container 300 through pipe 307, second buffer container 306 or pipe 307 or tube 106 is optionally connected with a water inlet pipe 400 for adding water to the water circuit formed by water bath 105, tube 111, pipe 307, optionally second buffer container 306, and pipe 106. This allows for concentrating the larvae suspension entering the buffer container 300 via pipe 111, relative to the larvae density in water bath 105, and re-using the water retrieved from the more diluted larvae suspension made in water bath 105, for transporting the water back to water bath 105. The concentrated larvae in buffer container 300 can be further transported via outlet 128 to tube 129. Water inlet pipe 400 for adding external water to the circuit and to the second buffer container 306 is provided with a valve 401, for controlling the amount and flow of water that flows to water bath 105. Thus, this way, a closed circuit for circulating water from water bath 105 up to buffer container 300 and back to water bath 105 is established, optionally through second water buffer container 306.

The amount of water collected in receptacle 306 is sufficient and enough for resuspending the filtered larvae 402 after filtration through filter 304, at the desired ratio. For resuspending the filtered larvae 402 in the re-used water from receptacle 306, receptacle 306 is in fluid communication with tube 111 through pipe 305 and connector 305' connecting pipe 305 with tube 111 at a location downstream from filter 304 and water outlet connector 307' and downstream from the means for determining larvae mass or volume 407. Once filtered larvae 402 are resuspended in the determined and controlled amount of water from receptacle 306, the provided larvae suspension 403 is delivered to the buffer container 300 through connector 127.

In an embodiment, the pipe 305 is optionally provided with a water cooling unit 303 for optionally cooling of the water provided from the tube 111 to the water bath 105 and into pipe 307 and optionally into buffer container 306, for example to a selected temperature of the range between about 10° C. and about 20° C. This way, water is re-usable efficiently. This way, the size of the buffer container 300 is smaller than the required size when unfiltered larvae would have been stored in more diluted suspension. This way, processing of suspended larvae 403 after transportation through tube 129 is made more energy-efficient (required less energy): less volume needs to be processed, keeping and heating/cooling and controlling water temperature at a desired value (typically about 20° C. prior to processing of the larvae) requires less energy due to the smaller total (water) volume.

Therefore, in an embodiment, the pipe 307 and/or the tube 106 and/or the pipe 305 is thus optionally provided with a filter means 302 for freeing the water from any solid matter 122 suspended therein. The filter means 302 is for example a filter, a sieve, a gauze, a maze, a net, with openings sufficiently small to hold the solid matter 122, while water is flowing through pipe 307, pipe 305 and tube 106, thus through filter means 302. Solid matter 122 is discarded from the filter means 302.

In an embodiment, buffer container 306 and pipe 305 form a closed water circuit through additional pipe 305", such that pipe 305 is in fluid connection with buffer container 306 through two connecting pipes. In a further embodiment, the water temperature controller 303 such as a water cooling unit 303 is part of the circuit formed by buffer container 306, pipe 305 and pipe 305". This way, water in buffer container 306 is brought at a predetermined and desired set temperature, e.g. cooled to 10° C.-14° C. if required, such that water at a predetermined and desired set temperature is provided to water bath 105.

In an exemplary embodiment, the water circuit is for example provided with a valve 312 for controlling the amount and flow velocity of water exiting buffer container 306 into pipe 305, for resuspending filtered larvae 402. Optionally, the water circuit is for example provided with a driver means 405 such as a pump, for controlling the amount and flow velocity of water exiting buffer container 306 into pipe 305, for resuspending filtered larvae 402, although alternatively static flow and water pressure is sufficient for inducing water flow back to connector 305'. Optionally, pipe 305 is for example provided with a valve 406 for controlling the amount and flow velocity of water exiting buffer container 306 into pipe 305, for resuspending filtered larvae 402. Optionally, the water circuit is for example provided with a valve 404, for controlling the amount and flow velocity of water exiting buffer container 306 into pipe 305 and re-entering buffer container 306 through pipe 305", optionally after being cooled with water temperature controller 303 such as a cooler 303. The water entering buffer container 306 through pipe 308, optionally mixed with water entering buffer container 306 through pipe 305", and optionally mixed with water provided through water inlet 400 and valve 401, is exiting buffer container 306 through connected pipe 106, under control of valve 308'. This way, water circulates from water bath 105 through pipe 111 through larvae separation means 304 into pipe 307, optionally into water buffer container 306, and into pipe 106, and finally back into water bath 105. Part of the water entering pipe 307 flows back through pipe 305 to connector 305' into buffer container 300.

Figure 1G:
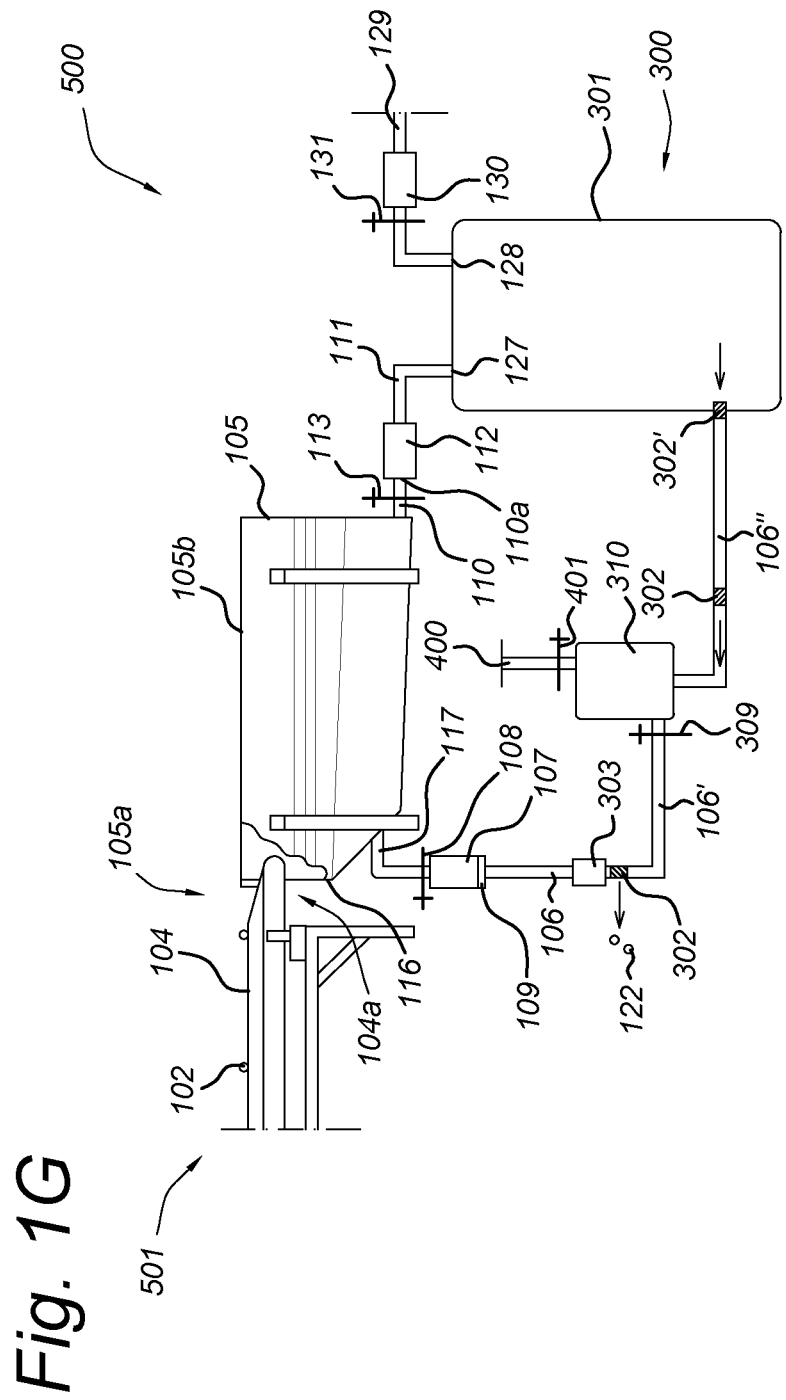

An embodiment of an assembly 500 for transporting and storing larvae at varying transport- and storing liquid to larvae mass (:) mass ratio or volume (:) volume ratio is shown in FIG. 1G. The assembly 500 is composed of a means 501 for delivering larvae 102 into water bath 105, such as a crate 120 or a conveyer unit 104; the water bath 105; suspension outlet unit 110-113 encompassing pipe 111, connector 127, buffer container 300, filter unit 302', pipe 106", filter(s) 302, optional second buffer container 310 provided with pipe 400 comprising valve 401 for water supply, pipe 106', cooler 303, pipe 106, optional water inlet control unit 107, valve 108, driver 109, water inlet opening 117, and outlet 128, valve 131, driver 130, pipe 129, as here above outlined when describing the embodiments depicted in FIGS. 1A, B, C, D and E.

The assembly 500 allows for transporting suspended larvae from water bath 105 to buffer container 300 at a more diluted ratio (ratio larvae (:) water is for example 1:7 to 1:50), compared to the storage of the larvae at a more concentrated ratio in buffer container 300, for example at a ratio of 1:1 to 1:6. At the same time, the assembly allows for efficient re-use of part of the water initially used for transferring suspended larvae from the water bath 105 to the buffer container 300, by partly recirculating the water back to the water bath 105, while more concentrated larvae suspension is subsequently transferred further through outlet 128 into pipe 129, with the remainder of the water. With assembly 500, the larvae density (by weight relative to the transport water, or by volume relative to the transport water) in the larvae suspension is adjustable and controllable according to the needs for transporting to buffer container 300 and to the needs for storage in the buffer container 300 and subsequent transport to for example a larvae processing unit. By controlling valve 309 and/or driver 107 and/or valve 108, the larvae density in the larvae suspension in water bath 105 and pipe 111 and in buffer container 300 can be set to a desired and pre-determined value, independently, by the presence of water inlet 400 under control of valve 401.

Figure 1H:
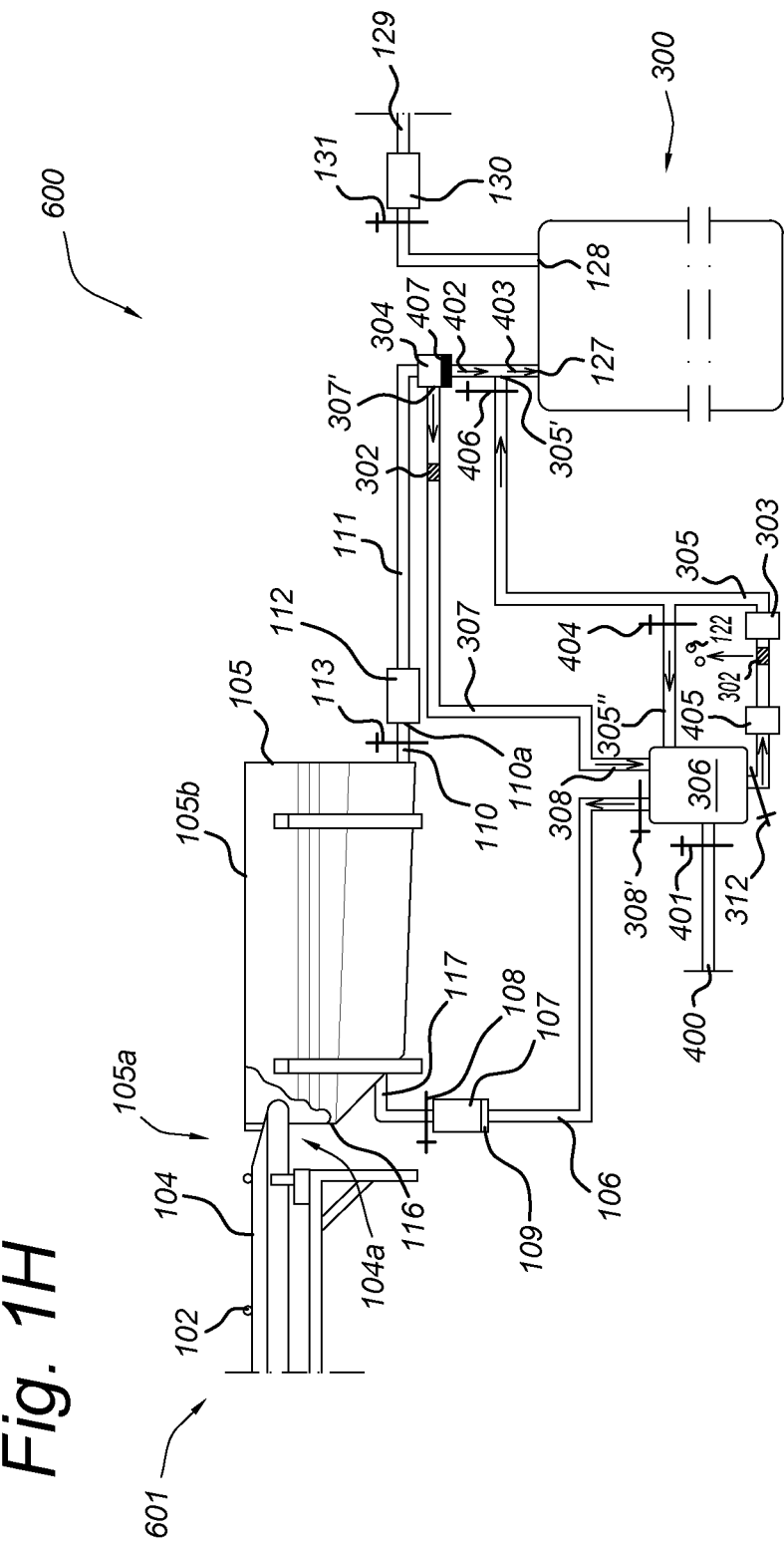

An embodiment of an assembly 600 for transporting and storing larvae at varying transport- and storing liquid to larvae mass (:) mass ratio or volume (:) volume ratio is shown in FIG. 1H. The assembly 600 is composed of a means 601 for delivering larvae 102 into water bath 105, such as a crate 120 or a conveyer unit 104; the water bath 105; suspension outlet unit 110-113 encompassing pipe 111, larvae separation means 304, means 407 for determining the weight and/or volume of larvae separated from the larvae suspension in water bath 105, connector 307' connecting pipe 111 with pipe 307, filter unit 302, connector 308, buffer container 306, pipe 305 comprising optional valve 312, optional driver 405, optional filter 302, optional cooler 303, optional valve 404 and pipe 305", and connector 305', connecting pipe 307 via pipe 305 with buffer container 300, said buffer container provided with outlet 128, for connecting with pipe 129 which comprises valve 131 and driver 130; buffer container 306 connected with pipe 400 comprising valve 401, for supplying water to buffer container 306, the buffer container 306 connected with pipe 106 comprising valve 308', optional water inlet control unit 107, valve 108, driver 109, water inlet opening 117 connected to water bath 105, as here above outlined when describing the embodiments depicted in FIGS. 1A, B, C, D and F.

The assembly 600 allows for transporting suspended larvae from water bath 105 up to larvae separation unit 304 positioned upstream from buffer container 300, at a more diluted ratio (ratio larvae (:) water is for example 1:7 to 1:50), compared to the storage of the larvae at a more concentrated ratio in buffer container 300, for example at a ratio of 1:1 to 1:6. At the same time, the assembly allows for efficient re-use of part of the water initially used for transferring suspended larvae from the water bath 105 up to the buffer container 300, by partly recirculating the water back to the water bath 105, while more concentrated larvae suspension 403 is subsequently transferred further through outlet 128 into pipe 129, with the remainder of the water.

With assembly 600, the larvae density (by weight relative to the transport water, or by volume relative to the transport water) in the larvae suspension exiting water bath 105 is initially adjustable and controllable according to the needs for transporting to buffer container 300 and subsequently and additionally to the needs for storage in the buffer container 300 and subsequent transport to for example a larvae processing unit. By controlling valve 308' and/or driver 107 and/or valve 108, the larvae density in the larvae suspension in water bath 105 and pipe 111 and in larvae separation unit 304 can be set to a desired and pre-determined value, independently, also by the presence of water inlet 400 under control of valve 401. By controlling valve 312 and/or driver 405 and/or valve 404 and/or valve 406, the larvae density in the larvae suspension 403 entering buffer container 300 through connector 127 and exiting buffer container through connector 128 (e.g. after storage for 10 minutes-2 days) can be set to a desired and pre-determined value, independently, also by the presence of water inlet 400 under control of valve 401. In addition, water temperature control unit 303, such as a water cooler 303, ensures optional provision of temperature control for the larvae suspension in water bath 105 and for the larvae suspension 403 in buffer container 300.

Of course the liquid applied for transporting and storing larvae is any liquid suitable for the purpose of keeping larvae alive and undamaged during transport and storage, such as a physiological (salt) solution, a buffer solution, mineralized water, etc., although water is preferred.

The present invention has been described above with reference to a number of exemplary embodiments as shown in the drawings. Modifications and alternative implementations of some parts or elements are possible, and are included in the scope of protection as defined in the appended claims. The invention is not limited in any way to the illustrated exemplary embodiments.

The invention claimed is:

1. Connector assembly for converting a batch wise supply of live insects to a continuous supply of live insects, comprising
   a container unit having an internal volume, a water inlet unit, and a suspension outlet unit,
   a receiving unit having a top opening arranged for receiving batch wise quantities of live insects and a bottom opening, and
   a conveyor unit having a receiving part arranged near the bottom opening of the receiving unit, and an outlet end extending into the container unit, wherein the conveyor unit further comprises a weighing device arranged underneath the receiving unit, and wherein the receiving unit is arranged on the weighting device for measuring the quantity of insects in the receiving unit.

2. The connector assembly according to claim 1, wherein the conveyer unit further comprises a scraper device positioned near the outlet end.

3. The connector assembly according to claim 1, wherein the water inlet unit comprises a water inlet control unit connected to the weighing device and arranged to control an amount of water supplied to the container unit based on measurement data from the weighing device.

4. The connector assembly according to claim 1, wherein the suspension outlet unit comprises a pumping device.

5. The connector assembly according to claim 1, wherein the container unit comprises an inlet opening and a suspension outlet opening which are arranged asymmetrically with respect to a bottom part of the container unit.

6. The connector assembly according to claim 1, wherein the container unit provides agitation in the internal volume of the container unit.

7. The connector assembly according to claim 1, wherein the container unit comprises an insect spreading element.

8. System for converting a batch wise supply of insects to a continuous supply of insects, comprising a connector assembly comprising:
   a container unit having an internal volume, a water inlet unit, and a suspension outlet unit
   a receiving unit having a top opening arranged for receiving batch wise quantities of live insects and a bottom opening, and
   a conveyor unit having a receiving part arranged near the bottom opening of the receiving unit, and an outlet end extending into the container unit, and
   wherein the system further comprises:
   a separation unit positioned near the top opening of the receiving unit, the separation unit being arranged to provide batch wise quantities of insects to the receiving unit and to separate waste from the batch wise quantities of insects.

9. Method for converting a batch wise supply of insects to a continuous supply of insects, comprising
   providing batch wise quantities of insects,
   converting the batch wise quantities of insects into a continuous stream of insects,
   suspending the continuous stream of insects in water to obtain a suspension of insects in water,
   transporting the suspension of insects in water.

10. The method according to claim 9, further comprising controlling an input volume of water depending on the weight of insects to be suspended in the water.

11. The method according to claim 9, further comprising spreading the continuous stream of insects over a surface of the water.

12. The method according to claim 9, further comprising separating waste from the batch wise quantities of insects.

13. The method according to claim 9, further comprising agitating the suspension of insects in the water.

* * * * *